United States Patent [19]

Tuckey, Jr.

[11] Patent Number: 4,887,413

[45] Date of Patent: Dec. 19, 1989

[54] BULK SAMPLER TOOL

[76] Inventor: Robert W. Tuckey, Jr., 9936 Woodfern Rd., Philadelphia, Pa. 19115

[21] Appl. No.: 199,052

[22] Filed: May 26, 1988

[51] Int. Cl.⁴ .............................................. B65B 63/00
[52] U.S. Cl. ...................................... 53/520; 53/435; 53/284; 408/68; 73/864.44
[58] Field of Search ................ 408/67, 68; 73/864.44, 73/864.45; 141/130, 74; 53/471, 435, 520, 49, 281, 284

[56] References Cited

U.S. PATENT DOCUMENTS

| | | | |
|---|---|---|---|
| 983,810 | 2/1911 | Crossley | 408/68 |
| 1,563,887 | 12/1925 | Wiespetat . | |
| 2,346,220 | 4/1944 | Kienzle et al. | 408/67 X |
| 3,978,733 | 9/1976 | Avot | 408/68 X |
| 4,126,081 | 11/1978 | Zdeb | 408/67 X |
| 4,289,252 | 9/1981 | Helms | 220/306 X |
| 4,657,445 | 4/1987 | Bossler . | |
| 4,662,802 | 5/1987 | Österman | 408/67 |

FOREIGN PATENT DOCUMENTS

| | | | |
|---|---|---|---|
| 1543043 | 10/1968 | France | 73/864.44 |
| 1559235 | 3/1969 | France | 73/864.44 |

Primary Examiner—Z. R. Bilinsky
Assistant Examiner—R. Schultz

[57] ABSTRACT

A tool for sampling building materials for the suspected presence of asbestos fibers. An annular (tubular) cutter element is rotated to remove a plug-like sample from a wall under study. A shroud-like canister surrounds the cutter element to trap any asbestos fiber particulates that might otherwise escape into the atmosphere. Closure caps can be applied to the canister, whereby the canister can be used to ship (transport) the sample to a laboratory for analysis.

2 Claims, 1 Drawing Sheet

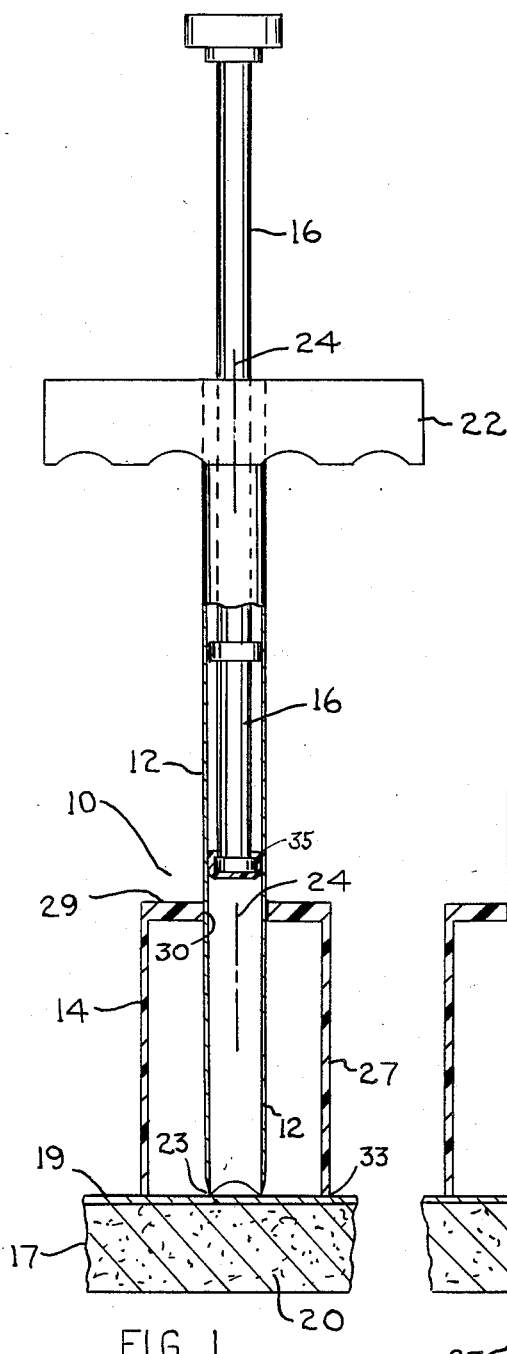
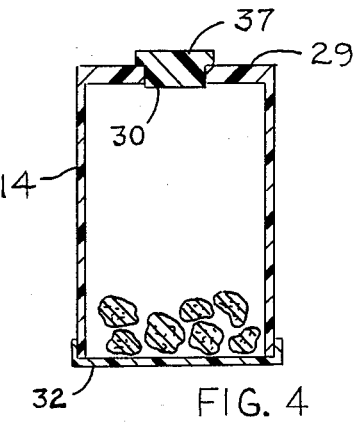
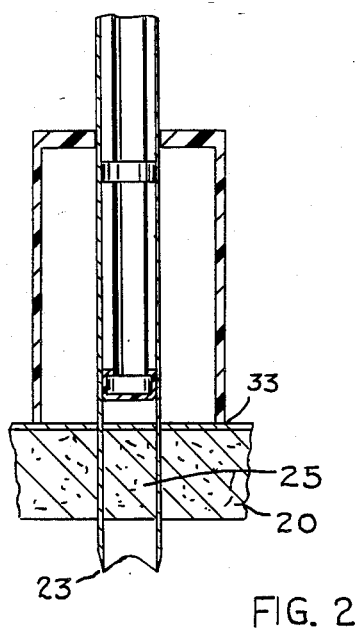
FIG. 1
FIG. 2
FIG. 3
FIG. 4

BULK SAMPLER TOOL

BACKGROUND OF THE INVENTION

It is known that airborne asbestos fibers can cause lung cancer, mesothelioma and other related diseases. For this reason the use of asbestos in building construction and consumer products is no longer permitted. However, there are many older buildings where asbestos is a built-in potential hazard.

Asbestos has been used in a variety of different items, e.g. insulation around pipes and heating ducts, paints, floor tiles, cement, shingles, spackling compounds, fabrics, and road-surfacing coatings. In the past, interior ceilings of school buildings and municipal buildings were often sprayed with asbestos-containing materials for decorative and fireproofing purposes. Over the passage of time asbestos fibers can be released from their entrapped states within (on) building wall surfaces into the air, where they pose a health hazard.

There is a need for a sampling tool that can be used to extract a small sample of material from a building wall (e.g. ceiling, vertical wall or floor) to test for the presence of asbestos fibers.

SUMMARY OF THE INVENTION

My invention relates to an asbestos sampling tool that comprises an annular cutter element designed to bore into a building wall ceiling or building material to remove a small plug-like section, e.g. a plug section only about one fourth inch in diameter and of the same thickness as the thickness of the material from which the sample is taken.

My tool is designed to include a small annular canister in surrounding relation to the cutter element, whereby fragments generated by the cutting operation are confined or contained within the canister.

My tool also includes a plunger-type ejector locatable within the annular cutter element to force the plug-like sample from the annular cutter into the canister. Closure caps are provided to seal the plug-like sample (and associated fragments) within the canister, whereby the canister can be transported to a laboratory for analyses of the asbestos level (content).

A primary aim of my invention is to provide a sampling tool wherein fragments generated during the cutting operation are trapped within an enveloping canister, rather than being dispersed into the atmosphere. This will protect the technician (building inspector) from inadvertent inhalation of asbestos fibers or skin contact with asbestos fibers.

Another object of my invention is to provide a sampling tool which can be used to sample a constant building wall area during each sampling operation, whereby meaningful comparative test results can be achieved.

A further object is to provide a sampling tool that captures substantially all of the asbestos contained in a given unit test area, thereby offering assurance as to the validity of the sampling technique.

Another object is to provide a sampling tool that can be used to obtain and package an individual sample in a comparatively short period of time, thereby enabling the technician to obtain more samples per visit to the building site being inspected.

THE DRAWINGS

FIG. 1 is a sectional view taken through a tool embodying my invention.

FIG. 2 is a fragmentary view taken in the same direction as FIG. 1, but illustrating the tool after it has penetrated a building material for obtaining a test sample.

FIG. 3 illustrates the tool while the test sample (plug) is being forced from the annular cutter into the associated canister.

FIG. 4 shows the canister with a test sample sealed therein for shipment to a testing laboratory.

DESCRIPTION OF A PREFERRED EMBODIMENT OF THE INVENTION

FIG. 1 shows a sampling tool 10 that includes an annular (tubular) cutter element 12, an annular cup-like canister 14, and a sample ejector 16. The tool is shown with the cutting edge of cutter element 12 in contact with a building wall 17 suspected to have asbestos fibers in its outer paint layer 19 or within the wall mass 20. Cutter element 12 is shown connected to a bar-like handle element 22.

Cutter element 12 is a cylindrical metal tube having a sharpened lower end edge 23 engageable with the building wall surface Annular edge 23 has an endless (continuous) wave-like configuration as seen in FIGS. 1 and 2. The cutter wave edge comprises a plural number of connected concave and convex curved edges that form one continuous wave shape around the tube circumference. The curved sections form a smooth edge surface devoid of abrupt shoulders or changes in direction.

In use of cutter element 12, handle 22 is manually grasped with one hand and turned around tube axis 24. Sharpened edge 23 dugs into building wall 20 to form an annular groove in the wall 20 surface. Eventually sharpened edge 23 cuts completely through the wall 20 thickness to sever a plug-like sample 25 from the wall (See FIG. 2).

The smoothly curved nature of cutting edge 23 is advantageous in that fragmentation of the wall 20 mass into small particulates is minimized. However, inevitably some particulates will be generated (the wall is usually plasterboard or drywall that is friable in nature). Canister (shroud) 14 is provided to contain (confine) dust and larger particulates generated during the wall cutting process.

Canister 14 comprises an annular (cylindrical) side wall 27, and an end wall 29 extending across one end of wall 27. Wall 27 has a circular opening 30 mated to tubular wall 12, whereby wall 12 can be rotated by application of manual force to handle 22 while the technician uses his other hand to hold canister 14 in a stationary position against the surface of wall 20. Canister 14 traps dust and other loose particulates that might be generated as cutting edge 23 penetrates the building wall surface.

Wall 20 is usually a vertical wall or an overhead wall (ceiling). When tubular cutter 12 is drawn back into canister 14 to the FIG. 3 position substantially all particulates are confined to the space circumscribed by the canister. A cap 32 can be applied to the open mouth end 33 of the canister to retain particulates within the canister.

The plug-like sample 25 can be forced from tubular cutter 12 into canister 14 by manual manipulation of aforementioned ejector 16. The ejector comprises a plunger 34 having a sock-like sealing element 35 as its lower end; element 35 is preferably formed of a plastic material having a smooth outer surface adapted to have a close sliding fit on the inner surface of tubular cutter 12, whereby downward motion of the plunger causes sample 25 to be forced downwardly out of tube 12 into canister 14. The sample may then fragment into separate particles, as shown in FIG. 4.

After the sample is forced from tube 12 into canister 14 the tube is lifted upwardly out of the opening in end wall 29. Thereafter a second closure (cap) 37 is fitted into opening 30 to seal the sample within the canister. The canister is preferably formed of a clear transparent material so that the user can see that it contains an extracted sample. A shipping identification label (not shown) can be adhesively applied to the canister outer surface to identify the sample as to building site (street and no., etc.) and location within the building.

Heretofore, asbestos sampling procedures (in older buildings) involved the use of knives and similar instruments designed to break off or cut out a reasonable amount of material for analysis. Inevitably some asbestos fibers became airborne or came into contact with the technician's clothing or skin. The present invention is designed to provide test samples of uniform size (e.g. plug-like samples having diameters of one fourth inch) for achievement of more meaningful test results. Another important objective is to permit the sampling procedure to be carried out without generating airborne particulates.

FIG. 1 of the drawing shows ejector 16 within tube 12. While tube 12 is being rotated to cut into the work (wall 17) ejector 16 can be removed from tube 12; however, if the ejector is left in tube 12 it will seal the tube against escape of dust particulates through the tube. The length and stroke of ejector 16 is largely determined by the expected thickness of the building wall to be analyzed; an ejector stroke length on the order of one inch would in most cases be sufficient.

The drawings show a hand-operated cutter 12. The cutter design could be modified for use in an electric drill; some changes in ejector design would be needed.

I claim:

1. A tool for removing and packaging a dry sample section from a building wall suspected of containing asbestos, comprising:

an annular cylindrical rotary cutter having an inner side surface and an outer side surface, a handle element (22) carried on said cutter, one end of said annular cutter remote from the handle element being sharpened for penetrating a building wall when a rotary actuating force is applied to the handle element, whereby a sample of the wall is received within a sample ejector located within the annular cutter to remove a sample from the cutter, said sample ejector comprising a plunger having a close sliding fit on the inner said surface of the cutter, the inner side surface of the cutter having a constant diameter over the entire length thereof traversed by the plunger so that sample fragments are prevented from adhering to side surface areas of the plunger or the cutter, said ejector extending out of the cutter to provide an external actuator section for manual movement of said plunger back and forth within the cutter;

an annular cup-like canister encircling said cutter; said canister comprising an imperforate annular side wall having an inner side surface spaced radially from the outer side surface of the cutter, said canister further including an end wall (29) extending across one end of the canister side wall;

said canister end wall having a circular opening therethrough mated to the outer side surface of the cylindrical cutter, such that the canister is capable of axial movement along the cutter to a position entirely removed from the cutter;

the canister side wall defining an open mouth adapted to engage the surface of a building wall while the cutter is being operated to cut into the wall material, the aforementioned radial spacing of the canister side wall and cutter side surface being such that a dust-reception space is formed between the cutter and canister;

a first relatively large diameter cap installable on the open mouth of the canister prior to operation of the ejector whereby the sample is ejected into the confined space defined by the first cap and the canister side wall;

and a second relatively small diameter cap installable in the circular opening in the canister end wall after the ejector has been operated to eject the sample into the canister, whereby the sample and associated fragments are sealed within the canister.

2. The tool of claim 1 wherein the canister is formed of a clear transparent plastic.

* * * * *